US012648740B2

(12) United States Patent
Kim et al.

(10) Patent No.: US 12,648,740 B2
(45) Date of Patent: Jun. 9, 2026

(54) METHOD, APPARATUS AND SYSTEM FOR PREDICTION OF NEONATAL BRAIN DEVELOPMENT PROGNOSIS

(71) Applicants: THE CATHOLIC UNIVERSITY OF KOREA INDUSTRY-ACADEMIC COOPERATION FOUNDATION, Seoul (KR); AJOU UNIVERSITY INDUSTRY-ACADEMIC COOPERATION FOUNDATION, Suwon-si (KR)

(72) Inventors: Hyun Gi Kim, Seoul (KR); Jang Hoon Lee, Suwon-si (KR)

(73) Assignees: THE CATHOLIC UNIVERSITY OF KOREA INDUSTRY-ACADEMIC COOPERATION FOUNDATION, Seoul (KR); AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 661 days.

(21) Appl. No.: 18/146,848

(22) Filed: Dec. 27, 2022

(65) Prior Publication Data

US 2023/0248263 A1     Aug. 10, 2023

(30) Foreign Application Priority Data

Feb. 9, 2022     (KR) ........................ 10-2022-0017161

(51) Int. Cl.
A61B 5/00          (2006.01)
A61B 5/026          (2006.01)
(Continued)

(52) U.S. Cl.
CPC .......... A61B 5/7275 (2013.01); A61B 5/0263 (2013.01); A61B 5/055 (2013.01);
(Continued)

(58) Field of Classification Search
CPC   A61B 5/11; A61B 5/72; A61B 5/0263; A61B 5/7275; A61B 5/0042;
(Continued)

(56) References Cited

U.S. PATENT DOCUMENTS

2020/0302602 A1 *   9/2020   Parikh .................... G16H 30/40
2021/0267492 A1       9/2021   Fry et al.

FOREIGN PATENT DOCUMENTS

KR          10-2001398 B1     7/2019
WO       WO-2016081677 A1 *   5/2016   ....... G01R 33/56366

OTHER PUBLICATIONS

Kim, H. G., et al. "Multidelay arterial spin-labeling MRI in neonates and infants: cerebral perfusion changes during brain maturation." American Journal of Neuroradiology 39.10 (2018): 1912-1918. (Year: 2018).*

(Continued)

*Primary Examiner* — Sumati Lefkowitz
*Assistant Examiner* — Ryan P Potts
(74) *Attorney, Agent, or Firm* — Studebaker Brackett PLLC

(57)          ABSTRACT

A method, apparatus and system for prediction of a neonatal brain development prognosis, using a pregenerated brain neurodevelopment prediction model. The apparatus includes a computing device, which includes a memory; and at least one processor performing communication with the memory. The processor is configured to extract cerebral blood flow (CBF) and brain tissue relaxation times T1 and T2 from the input magnetic resonance imaging (MRI) of a subject newborn, generate brain neurodevelopment prediction data of the subject newborn using a pregenerated brain neurodevelopment prediction model, and control the output of the generated brain neurodevelopment prediction data of the subject newborn.

16 Claims, 10 Drawing Sheets

(51) Int. Cl.

| | |
|---|---|
| *A61B 5/055* | (2006.01) |
| *A61B 5/11* | (2006.01) |
| *G06T 7/00* | (2017.01) |
| *G16H 30/40* | (2018.01) |
| *G16H 50/30* | (2018.01) |
| *G16H 50/50* | (2018.01) |
| *G06N 20/00* | (2019.01) |

(52) U.S. Cl.

CPC .............. *A61B 5/11* (2013.01); *A61B 5/4064* (2013.01); *A61B 5/4088* (2013.01); *A61B 5/72* (2013.01); *A61B 5/7264* (2013.01); *G06T 7/0012* (2013.01); *G16H 30/40* (2018.01); *G16H 50/30* (2018.01); *G16H 50/50* (2018.01); *A61B 5/0042* (2013.01); *A61B 2503/045* (2013.01); *G06N 20/00* (2019.01); *G06T 2207/10088* (2013.01); *G06T 2207/20081* (2013.01)

(58) Field of Classification Search

CPC . A61B 2503/045; A61B 5/4064; A61B 5/055; A61B 5/4088; A61B 5/7264; A61B 6/501; G16H 30/40; G16H 50/30; G16H 50/50; G16H 10/60; G06T 2207/30016; G06T 2207/20084; G06T 2207/10088; G06T 7/0012; G06N 3/0464; G06N 20/00; G06N 3/045; G06N 3/08; G06N 3/09; G06N 3/02; G06N 3/0475; G06N 7/01; G06N 3/092; G06N 20/10; G06N 3/0895; G06N 5/04; G06N 3/084; G06N 3/0455; G06N 3/047; G06N 20/20; G06N 3/0499; G06N 3/096; G06N 3/094; G06N 3/091; G06N 5/048

See application file for complete search history.

(56) References Cited

OTHER PUBLICATIONS

Chen, Peiyao, et al. "Developmental Trajectories of Cerebral Blood Flow and Neurodevelopmental Score in Preterm Children from 28 Days to 13 Years." Ismrm.org, 2021, cds.ismrm.org/protected/21MProceedings/PDFfiles/1633.html. Accessed Jul. 9, 2025. (Year: 2021).*

Suman, Garima, et al. "Multidelay arterial spin labeling MRI in the assessment of cerebral blood flow: preliminary clinical experience in pediatrics." Pediatric Neurology 103 (2020): 79-83. (Year: 2020).*

Miller, Steven P., et al. "Early brain injury in premature newborns detected with magnetic resonance imaging is associated with adverse early neurodevelopmental outcome." The Journal of pediatrics 147.5 (2005): 609-616. (Year: 2005).*

Vanderhasselt, Tim, et al. "Synthetic MRI demonstrates prolonged regional relaxation times in the brain of preterm born neonates with severe postnatal morbidity." NeuroImage: Clinical 29 (2021): 102544. (Year: 2021).*

Zheng, Qiang, et al. "Cerebral pulsed arterial spin labeling perfusion weighted imaging predicts language and motor outcomes in neonatal hypoxic-ischemic encephalopathy." Frontiers in Pediatrics 8 (2020): 576489. (Year: 2020).*

Bos, A.F. (2013), Bayley-II or Bayley-III: what do the scores tell us?. Dev Med Child Neurol, 55: 978-979. (Year: 2013).*

Celik, Pelin, Iclal Ayranci Sucakli, and Halil Ibrahim Yakut. "Which Bayley-III cut-off values should be used in different developmental levels?." Turkish journal of medical sciences 50.4 (2020): 764-770. (Year: 2020).*

Kim et al.; Association of Cerebral Blood Flow and Brain Tissue Relaxation Time With Neurodevelopmental Outcomes of Preterm Neonates; Investigative Radiology; vol. 00, No. 00; Nov. 4, 2021.

An Office Action mailed by the Korean Intellectual Property Office on May 6, 2024, which corresponds to Korean Patent Application No. 10-2022-0017161 and is related to U.S. Appl. No. 18/146,848.

Kim Hyun Gi, "Advanced neuroimaging for quantitative assessment of neurodevelopment and prognosis prediction in preterm infants", (Science and Engineering Individual Basic Research Support Project) Final (Result) Report, Sep. 9, 2020, total 19 pages.

Qiang Zheng et al., "Cerebral Pulsed Arterial Spin Labeling Perfusion Weighted Imaging Predicts Language and Motor Outcomes in Neonatal Hypoxic-Ischemic Encephalopathy", Frontiers in Pediatrics, vol. 8, pp. 1-9, Sep. 25, 2020.

Kyoung Eun Lee et al., "Usefulness of Early Neurodevelopmental Testing for High-Risk Neonates", J Korean Child Neurol Soc 2018; vol. 26, No. 3, pp. 164-169, Sep. 2018.

* cited by examiner

| Characteristics | CBF Analysis | Relaxation Time Analysis |
|---|---|---|
| No. pretern neonates | 48 | 49 |
| Demographic | | |
| Gestational age at birth, d | 208 (15) | 209 (17) |
| Gestational age at birth, wk | 30 (2) | 30 (2) |
| Birth weight, g | 1240 (495) | 1230 (380) |
| Male sex | 27 (56.3%) | 28 (57.1%) |
| Cesarean delivery | 42 (87.5%) | 43 (87.8%) |
| Apgar score at 1 min | 4 (2) | 4 (2) |
| Apgar score at 5 min | 6 (3) | 6 (3) |
| Corrected gestational age at MRI scan, d | 258 (17) | 258 (14) |
| Corrected gestational age at MRI scan, wk | 37 (2) | 37 (2) |
| Sedation for MRI scan | 25 (52%) | 25 (51%) |
| Socioeconomic status | | |
| Maternal level of education | | |
| Primary/secondary | 16 (33.3%) | 17 (34.7%) |
| Under/postgraduate | 32 (66.7%) | 32 (65.3%) |
| Paternal level of education | | |
| Primary/secondary | 14 (29.2%) | 14 (28.6%) |
| Under/postgraduate | 34 (70.8%) | 35 (71.4) |
| Family income | | |
| <$3500/month | 25 (54.3%) | 26 (55.3%) |
| ≥$3500/month | 21 (45.7%) | 21 (44.7%) |
| Neurodevelopmental outcome | | |
| MDI score | 98 (16) | 96 (16) |
| PDI score | 96 (10) | 96 (10) |

Note: Values are n (%) or median (interquartile range).

CBF, cerebral blood flow; MRI, magnetic resonance imaging; MDI, Mental Development Index; PDI, Psychomotor Development Index.

FIG. 8

| | Median (IQR) | Gestation Age | | Corrected Gestation Age | |
|---|---|---|---|---|---|
| | | Coefficient | P | Coefficient | P |
| Cerebral blood flow, mL/100 g per min | | | | | |
| Frontal WM | 6.3 (4.9) | -0.07 | 0.657 | 0.59 | <0.001 |
| Occipital WM | 10.8 (7.1) | 0.07 | 0.635 | 0.44 | 0.002 |
| Frontal cortical GM | 24.0 (6.3) | -0.11 | 0.455 | 0.17 | 0.254 |
| Occipital cortical GM | 31.0 (9.9) | 0.00 | 0.979 | 0.31 | 0.031 |
| Caudate | 35.8 (14.8) | -0.06 | 0.686 | 0.48 | 0.001 |
| Thalamus | 42.9 (17.2) | 0.06 | 0.673 | 0.12 | 0.421 |
| Whole brain | 21.2 (6.8) | -0.06 | 0.686 | 0.48 | 0.001 |
| T1 relaxation time, ms | | | | | |
| Frontal WM | 2664 (119) | -0.19 | 0.199 | -0.53 | <0.001 |
| Occipital WM | 2417 (178) | -0.02 | 0.877 | -0.54 | <0.001 |
| Caudate | 1938 (83) | -0.06 | 0.666 | -0.65 | <0.001 |
| Putamen | 1792 (99) | -0.12 | 0.393 | -0.82 | <0.001 |
| Thalamus | 1816 (109) | 0.04 | 0.805 | -0.55 | <0.001 |
| Genu of corpus callosum | 2420 (306) | -0.08 | 0.580 | -0.54 | <0.001 |
| Middle cerebellar peduncle | 1542 (171) | 0.15 | 0.298 | -0.51 | <0.001 |
| Posterior limb of internal capsule | 1704 (108) | -0.10 | 0.482 | -0.86 | <0.001 |
| T2 relaxation time, ms | | | | | |
| Frontal WM | 304 (48) | -0.15 | 0.315 | -0.39 | 0.006 |
| Occipital WM | 256 (29) | -0.02 | 0.890 | -0.49 | <0.001 |
| Caudate | 180 (14) | 0.03 | 0.853 | -0.77 | <0.001 |
| Putamen | 161 (14) | -0.02 | 0.892 | -0.83 | <0.001 |
| Thalamus | 157 (13) | 0.08 | 0.577 | -0.64 | <0.001 |
| Genu of corpus callosum | 252 (49) | -0.07 | 0.640 | -0.48 | 0.001 |
| Middle cerebellar peduncle | 133 (16) | 0.17 | 0.252 | -0.52 | <0.001 |
| Posterior limb of internal capsule | 156 (12) | -0.05 | 0.712 | -0.82 | <0.001 |

IQR, interquartile range; WM, white matter; GM, gray matter.

FIG. 9

| | MDI | | | |
| | Simple Regression | | Multiple Regression | |
| | β (SE) | P | β (SE) | P |
|---|---|---|---|---|
| Cerebral blood flow, mL/100 g per min | | | | |
| Frontal WM | −1.04 (0.45) | 0.026 | −0.91 (0.43) | 0.029 |
| Occipital WM | −0.18 (0.38) | 0.633 | −0.25 (0.36) | 0.501 |
| Frontal cortical GM | −0.16 (0.32) | 0.634 | −0.07 (0.31) | 0.812 |
| Occipital cortical GM | −0.25 (0.25) | 0.333 | −0.25 (0.24) | 0.304 |
| Caudate | −0.18 (0.19) | 0.344 | −0.16 (0.18) | 0.384 |
| Thalamus | −0.02 (0.17) | 0.893 | −0.05 (0.16) | 0.770 |
| Whole brain | −0.60 (0.36) | 0.101 | −0.55 (0.34) | 0.114 |
| T1 relaxation time, ms | | | | |
| Frontal WM | 0.03 (0.02) | 0.102 | 0.03 (0.01) | 0.025 |
| Occipital WM | 0.02 (0.01) | 0.113 | 0.02 (0.01) | 0.084 |
| Caudate | −0.02 (0.03) | 0.477 | −0.01 (0.02) | 0.552 |
| Putamen | 0.02 (0.02) | 0.357 | 0.03 (0.02) | 0.198 |
| Thalamus | 0.03 (0.02) | 0.190 | 0.03 (0.02) | 0.197 |
| Genu of corpus callosum | −0.01 (0.01) | 0.567 | −0.00 (0.01) | 0.685 |
| Middle cerebellar peduncle | 0.03 (0.02) | 0.086 | 0.02 (0.01) | 0.150 |
| Posterior limb of internal capsule | 0.02 (0.02) | 0.221 | 0.02 (0.01) | 0.120 |
| T2 relaxation time, ms | | | | |
| Frontal WM | 0.05 (0.06) | 0.384 | 0.07 (0.06) | 0.197 |
| Occipital WM | 0.13 (0.07) | 0.079 | 0.13 (0.07) | 0.057 |
| Caudate | −0.03 (0.18) | 0.856 | −0.04 (0.17) | 0.797 |
| Putamen | 0.15 (0.18) | 0.388 | 0.16 (0.17) | 0.338 |
| Thalamus | 0.27 (0.21) | 0.217 | 0.23 (0.20) | 0.271 |
| Genu of corpus callosum | −0.04 (0.05) | 0.429 | −0.03 (0.05) | 0.506 |
| Middle cerebellar peduncle | 0.22 (0.18) | 0.226 | 0.15 (0.17) | 0.381 |
| Posterior limb of internal capsule | 0.19 (0.18) | 0.309 | 0.21 (0.17) | 0.228 |

β, beta coefficient; SE, standard error, WM, white matter; GM, gray matter, MDI, Mental Devlopment Index.

FIG. 10

| | PDI | | | |
| | Simple Regression | | Multiple Regression | |
| | β (SE) | P | β (SE) | P |
|---|---|---|---|---|
| Cerebral blood flow, mL/100 g per min | | | | |
| Frontal WM | −0.21 (0.41) | 0.603 | −0.16 (0.40) | 0.680 |
| Occipital WM | 0.25 (0.32) | 0.436 | 0.21 (0.32) | 0.503 |
| Frontal cortical GM | −0.16 (0.28) | 0.577 | −0.10 (0.27) | 0.713 |
| Occipital cortical GM | −0.07 (0.22) | 0.764 | −0.07 (0.21) | 0.752 |
| Caudate | −0.15 (0.16) | 0.368 | −0.13 (0.16) | 0.407 |
| Thalamus | −0.08 (0.14) | 0.602 | −0.09 (0.14) | 0.513 |
| Whole brain | −0.14 (0.32) | 0.655 | −0.11 (0.31) | 0.728 |
| T1 relaxation time, ms | | | | |
| Frontal WM | 0.01 (0.01) | 0.402 | 0.02 (0.01) | 0.218 |
| Occipital WM | 0.01 (0.01) | 0.281 | 0.01 (0.01) | 0.251 |
| Caudate | −0.00 (0.02) | 0.875 | −0.00 (0.02) | 0.964 |
| Putamen | 0.00 (0.02) | 0.915 | 0.01 (0.02) | 0.732 |
| Thalamus | 0.00 (0.02) | 0.860 | 0.00 (0.02) | 0.909 |
| Genu of corpus callosum | −0.01 (0.01) | 0.167 | −0.01 (0.01) | 0.205 |
| Middle cerebellar peduncle | 0.02 (0.01) | 0.118 | 0.02 (0.01) | 0.184 |
| Posterior limb of internal capsule | −0.00 (0.01) | 0.998 | 0.00 (0.01) | 0.852 |
| T2 relaxation time, ms | | | | |
| Frontal WM | −0.02 (0.05) | 0.724 | −0.01 (0.05) | 0.926 |
| Occipital WM | 0.07 (0.06) | 0.301 | 0.07 (0.06) | 0.272 |
| Caudate | −0.10 (0.15) | 0.505 | −0.11 (0.15) | 0.462 |
| Putamen | −0.03 (0.15) | 0.838 | −0.03 (0.15) | 0.862 |
| Thalamus | −0.03 (0.18) | 0.885 | −0.05 (0.18) | 0.764 |
| Genu of corpus callosum | −0.07 (0.04) | 0.086 | −0.07 (0.04) | 0.102 |
| Middle cerebellar peduncle | 0.17 (0.15) | 0.272 | 0.12 (0.15) | 0.409 |
| Posterior limb of internal capsule | −0.06 (0.16) | 0.695 | −0.05 (0.15) | 0.762 |

β, beta coefficient; SE, standard error, WM, white matter; GM, gray matter, PDI, Psyshomotor Devlopment Index.

METHOD, APPARATUS AND SYSTEM FOR PREDICTION OF NEONATAL BRAIN DEVELOPMENT PROGNOSIS

CROSS-REFERENCE TO RELATED APPLICATION

The present application is a claim for priority under 35 U.S.C. § 119, made to Korean Patent Application No. 10-2022-0017161, filed on Feb. 9, 2022, in the Korean Intellectual Property Office. The disclosures of the entire contents of which are hereby incorporated by reference.

BACKGROUND

1. Technical Field

The present disclosure relates to prediction of a brain development prognosis, in particular, a method, apparatus, and system for prediction of a neonatal brain development prognosis based on data regarding the neonatal brain using advanced imaging techniques and correlation with a neurodevelopment outcome.

2. Description of Related Art

Newborns, including preterm infants, are relatively vulnerable to neurodevelopmental disorders. Such neurodevelopmental disorders may be generally discovered after more than one year, and by then, there is the danger of delayed response, difficulty in providing treatment, or sequelae occurring.

Therefore, there is a need for diagnosis of whether a neonatal neurodevelopmental disorder is present.

Previously, Arterial Spin Labeling (ASL) was used to measure cerebral perfusion. However, there has been difficulty measuring cerebral perfusion using ASL because the newborn brain is relatively small, and the relaxation times of blood and brain tissues are different.

With regard thereto, US Patent Publication US 2021-0267492A1 (Sep. 2, 2021) relates to a system and method of detecting motor development delay or neurodevelopmental disorder, which includes technology that integrates sensors in an infant's clothing and detects motion in the femoral and cnemis, and analyzes neurodevelopmental disorders. This technology includes detecting early neurodevelopmental disorders in infants. However, it does not disclose a technology for predicting neurodevelopment based on neuroimaging.

SUMMARY

An object of the present disclosure is to provide data related to neonatal brains using advanced imaging techniques and correlation to a neurodevelopmental outcome.

Another object of the present disclosure is to provide neurodevelopmental outcomes of newborns, including premature infants, i.e., a method, apparatus and system for prediction of a prognosis.

The aspects of the present disclosure are not limited to those mentioned above, and other aspects not mentioned herein will be clearly understood by those skilled in the art from the following description.

To accomplish the above-mentioned objects, according to an aspect of the present disclosure, provided is a computing device including a memory; and at least one processor communicating with the memory; wherein the processor is configured to extract cerebral blood flow (CBF) and brain tissue relaxation times T1 and T2 from the input magnetic resonance imaging (MRI) of a subject newborn; generate brain neurodevelopmental prediction data of a subject newborn using a pregenerated brain neurodevelopmental prediction model; and control the output of the brain neurodevelopmental prediction data generated from the subject newborn.

A system for prediction of a prognosis of brain neurodevelopment according to an aspect of the present disclosure includes a terminal requesting brain neurodevelopmental prognosis of a subject newborn; and a computing device; wherein the computing device includes a processor which extracts the relaxation times T1 and T2 of CBF and brain tissues from the input MRI of a subject newborn; generates grain neurodevelopmental prediction data of the subject newborn using a pregenerated brain neurodevelopmental prediction model; and controls the output of the brain neurodevelopmental prediction data generated from the subject newborn.

A method for prediction of a prognosis of brain neurodevelopmental performed by a device according to an aspect of the present disclosure includes operations of: receiving magnetic resonance imaging (MRI) of a subject newborn; extracting CBF and brain tissue relaxation times T1 and T2 from the received MRI of the subject newborn; generating brain neurodevelopmental prediction data of the subject newborn using a pregenerated brain neurodevelopmental prediction model; and controlling the output of the generated brain neurodevelopmental prediction data of the subject newborn.

Other detailed features of the present disclosure are included in the Detailed Description and the Drawings.

BRIEF DESCRIPTION OF THE DRAWINGS

FIG. 5 is a diagram schematically illustrating cerebral blood flow (CBF) according to an exemplary embodiment of the present disclosure.

FIG. 7 to FIG. 10 are diagrams schematically illustrating data related to brain neurodevelopment prediction according to the present disclosure.

DETAILED DESCRIPTION

Figure 1:
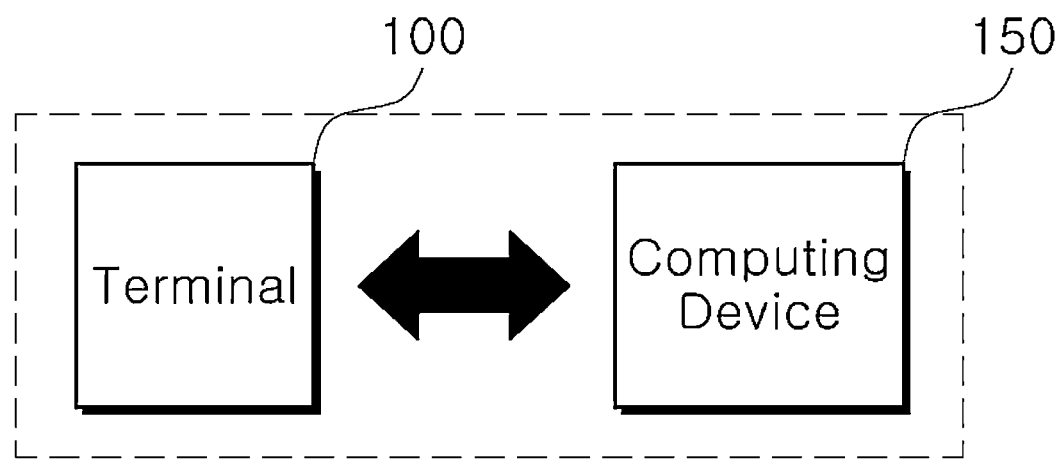
FIG. 1 is a diagram schematically illustrating a system for predicting brain neurodevelopment according to an embodiment of the present disclosure.

Advantages and features of the present disclosure and methods accomplishing the advantages and features will become apparent from the following detailed description of exemplary embodiments with reference to the accompanying drawings. However, the present disclosure is not limited to exemplary embodiment disclosed herein but will be implemented in various forms. The exemplary embodiments are provided so that the present disclosure is completely disclosed, and a person of ordinary skilled in the art can fully understand the scope of the present disclosure. Therefore, the present disclosure will be defined only by the scope of the appended claims.

Terms used in the specification are used to describe specific embodiments of the present disclosure and are not intended to limit the scope of the present disclosure. In the specification, the terms of a singular form may include plural forms unless otherwise specified. It should be also understood that terms such as 'comprises' or 'including' in the specification are used to mean that there is no intent to exclude the existence or addition of other components besides components described in the specification. In the detailed description, the same reference numbers of the drawings refer to the same or equivalent parts of the present disclosure, and the term "and/or" is understood to include a combination of one or more of the components described above. It will be understood that terms, such as "first" or "second," may be used in the specification to describe various components but are not restricted to the above terms. The terms may be used to discriminate one component from another component. Therefore, of course, the first component may be named as the second component within the scope of the present disclosure.

Unless otherwise defined, all terms (including technical and scientific terms) used herein have the same meaning as commonly understood by those skilled in the technical field to which the present disclosure pertains. It will be further understood that terms, such as those defined in commonly used dictionaries, should not be interpreted in an idealized or overly formal sense unless expressly so defined herein.

Spatially relative terms such as "below," "beneath," "lower," "above," and "upper" may be used to easily describe the correlation of one component with other components as schematically illustrated in the drawings. The spatially relative terms must be understood as encompassing different orientations of components in use or operation in addition to the directions shown in the drawings. For example, in case the components illustrated in the drawings are turned upside down, the components described as "below" or "beneath" another component may be placed "above" the other component. Therefore, an exemplary term "below" may include both above and below. Components may be oriented in other directions, and thus the spatially relative terms may be interpreted according to orientation.

Hereinafter, preferred embodiments of the present disclosure will be described in detail with reference to the accompanying drawings.

In the present specification, the apparatus for prediction of a brain development prognosis of newborns including premature infants, according to an embodiment of the present disclosure includes all various devices capable of providing results to the users by performing computational processing. For example, the apparatus for prediction of a brain development prognosis according to an embodiment of the present disclosure may include a computer, a server device, a mobile terminal, or maybe any one form.

Here, the computer, for example, includes a laptop device with a Web browser, a desktop, a tablet PC, and a slate PC. The server device as a server that processes information by performing communicating with external devices includes an application server, a computing server, a database server, a file server, a game server, a mail server, a proxy server, and web server. The portable terminal, for example, as a wireless communications device that ensures portability and mobility may include all types of handheld-based wireless communications devices such as a Personal Communication System (PCS), a Global System for Mobile communications (GSM), a Personal Digital Cellular (PDC), a Personal Handy-phone System (PHS), a Personal Digital Assistant (PDA), an International Mobile Telecommunication (IMT)-2000, a Code Division Multiple Access (CDMA)-2000, a W-Code Division Multiple Access (W-CDMA) or a Wireless Broadband (WiBro) Internet terminal, or a Smartphone, and may include wearable devices such as a watch, ring, bracelet, anklet, necklace, glasses, contact lenses, a head-mounted-device (HMD) or the like.

The neonatal brain development prediction model or prediction platform according to an embodiment of the present disclosure may be generated and provided by a computing device based on Big Data and Artificial Intelligence technology, and may be embodied by using or referencing Extended Reality (XR) which collectively refers to Virtual Reality (VR), Augmented Reality (AR), Mixed Reality (MR); and Information and Communication Technology (ICT) such as Block-chain technology for security of medical information or personal information included therein. In the present specification, a detailed description of the ICT technology according to an embodiment of the present disclosure may be referred to as a known technology. Therefore, a separate description thereof is omitted.

A neurodevelopmental disorder is one of the complications in high-risk newborns, including premature infants. The need for an early diagnosis of neonatal neurodevelopment is emphasized because if not appropriately treated at an appropriate time, a developmental delay may accelerate to develop into a disability.

However, neonatal brain size is relatively small and the relaxation times of blood and brain tissues are different, so it is challenging to measure cerebral perfusion using Arterial Spin Labeling (ASL). For this reason, a neonatal neurodevelopmental disorder is often found after one year.

Therefore, in one embodiment of the present disclosure, it is intended to provide a prediction model or a platform (hereafter, model) capable of predicting a prognosis of brain neurodevelopment in target newborns by using the Multidelay ASL to measure neonatal Cerebral Blood Flow (CBF), which is generally known to indicate the maturity of a neonatal brain, while reflecting the characteristics of the relaxation time of the brain tissues. Therefore, according to one embodiment of the present disclosure, the neurodevelopmental outcome may be predicted at an earlier time as compared to the conventional technology, therefore, a response may be made in a timely manner so that the damage or sequelae caused by neurodevelopmental disorders may be eliminated or minimized.

In particular, relating to the neonatal brain neurodevelopmental prediction model previously described in an embodiment of the present disclosure, relaxation time data of the neonatal CBF may be obtained by using Multidelay ASL and (synthetic) Magnetic Resonance Imaging (MRI), and by verifying the correlation to the subsequent neurodevelopmental outcomes.

On the other hand, the Multidelay ASL used in the present disclosure is disclosed as using an ASL Hadamard encoding method, but the present disclosure is not limited thereto.

Furthermore, in the present specification, the basic operational principles such as Multidelay ASL and MRI used in the present disclosure may be referred to known technology. Therefore, a separate description thereof is omitted.

The disclosure described in the present specification exemplifies newborns, including premature infants to generate a brain neurodevelopmental prediction model. However, the present disclosure is not limited thereto. Various exemplary embodiments of the present disclosure may be used in the medical field, such as neurodevelopment prognosis for young children, as well as newborns.

Additionally, the present disclosure further includes one or more factors related to brain neurodevelopment that may be discovered or known later, which may improve the accuracy and efficacy of the brain neurodevelopmental prediction model.

FIG. 1 is a diagram schematically illustrating a system for predicting brain neurodevelopment according to an embodiment of the present disclosure.

Figure 2:
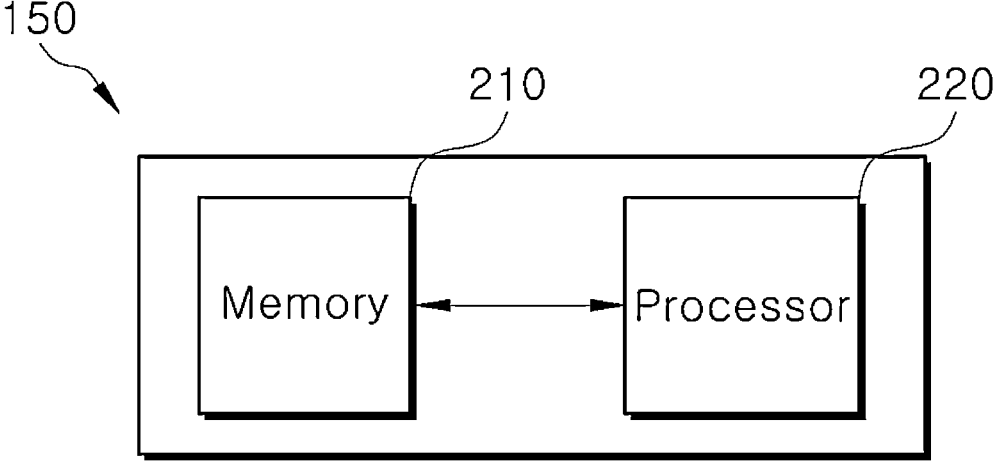
FIG. 2 is a configuration block diagram of the computing device illustrated in FIG. 1.

FIG. 2 is a configuration block diagram of the computing device illustrated in FIG. 1.

Referring to FIG. 1, the neonatal brain neurodevelopment prediction system according to an embodiment of the present disclosure may be configured to include a terminal 100 and a computing device 150.

According to an embodiment of the present disclosure, the system for predicting brain neurodevelopment, relating to performing an operation according to the present disclosure, may be configured to include one or more components other than the components illustrated in FIG. 1.

According to an embodiment of the present disclosure, as illustrated in FIG. 1, illustrates a terminal 100 which requests brain neurodevelopmental prediction service, and the computing device 150 which receives and processes the terminal which requests a brain neurodevelopmental prediction service of the terminal 100 as separate configurations, but the present disclosure is not limited thereto.

For example, the terminal 100 for the brain neurodevelopmental prediction service and the computing device 150 may be realized as one device. In this case, the computing device 150 which directly performs the brain neurodevelopmental prediction service may be modularized to be a component of the terminal 100, or be performed by a hardware configuration of the terminal 100 in software forms such as application or program.

However, in the present specification, the terminal 100 for predicting brain neurodevelopment and the computing device 150 are described as separate devices.

A terminal 100 requests the brain neurodevelopmental prediction of a subject newborn. Here, the User Interface (UI) (for example, provided by the computing device 150) for requesting the brain neurodevelopment prediction request of the subject newborn is output on the output interface of a terminal 100, and the request may be performed by using thereof.

A terminal 100 may upload the reference data used for the brain neurodevelopment prediction of the subject newborn.

The terminal 100 may output the result data of the brain neurodevelopment prediction from the computing device 150 thereafter.

A computing device 150 may receive and process the brain neurodevelopment prediction from the terminal 100, and generate outcome data to return to the terminal 100. Here, the brain neurodevelopment prediction request terminal and the terminal 100 for receiving and outputting outcome data may differ.

Referring to FIG. 2, the computing device 150 may be configured to include a memory 210 and a processor 220.

Here, the memory 210 may store all or at least a portion of the data received and processed in the computing device 150 described in the present specification.

This memory 210 may be an attachment to the computing device 210 as a component, as well as being located remotely which is interlocked or connected to each other. Also, only one memory 210 is exemplified in FIG. 2, but the present disclosure is not limited thereto.

A computing device 150 may provide a service in which the brain neurodevelopment prediction model is applied according to an embodiment of the present disclosure in an application or a web service form. However, the present disclosure is not limited thereto.

According to an embodiment of the present disclosure, a computing device 150 generates a brain neurodevelopmental prediction model to predict the degree of brain neurodevelopment in a subject newborn, for this purpose, collects, stores and processes data from at least one internal/external source. At least one internal/external source may include, for example, a national agency server database related to domestic/overseas medical data, a professional medical institution server, or a medical thesis service provider server.

Referring to FIG. 2, a computing device 150 may further include a communication module (not illustrated) supporting data communications with the terminal 100, a source, etc. According to another exemplary embodiment of the present disclosure, a communication module may be realized as a component of the processor 220.

As described previously, the communication module may include at least one component which enables communications with external devices such as the terminal 100 or at least one source. For example, it may include at least one of a wired communication module, a wireless communication module, a short-range field communication module, location information module.

As described above, the wired communication module may include not only various wired communication modules such as a Local Area Network (LAN), a Wide Area Network (WAN), or a Value Added Network (VAN), but also various cable communication modules such as Universal Serial Bus (USB), High Definition Multimedia Interface (HDMI), Digital Visual Interface (DVI), recommended standard-232 (RS-232), power line communications, or Plain Old Telephone Service (POTS).

The wireless communication module may include wireless communication that supports various wireless communication methods such as global System for Mobile Communication (GSM), Code Division Multiple Access (CDMA), Wideband Code Division Multiple Access (WCDMA), universal mobile telecommunications system (UMTS), Time Division Multiple Access (TDMA), Long Term Evolution (LTE), Fourth Generation (4G), 5G, 6G, as well as a Wi-Fi module, Wireless broadband or the like.

The short-range communication module is to enable short-range communication and may support short-range communication by using at least one of technologies such as Bluetooth™, Radio Frequency Identification (RFID), Infrared Data Association (IrDA), Ultra-Wideband (UWB), Zig-Bee®, Near Field Communication (NFC), Wireless-Fidelity (Wi-Fi), Wi-Fi Direct, Wireless Universal Serial Bus (USB).

The location information module is, for example, is for obtaining the terminal 100 location (or current location), typical examples are Global Positioning System (GPS) module and a Wi-Fi module. As an example, when a GPS module is used, the terminal 100 location may be obtained by using a signal sent from a GPS satellite. As another example, when a Wi-Fi module is used, the device's location may be obtained based on the information of the Wi-Fi module and Wireless Access Point (AP) that transmits or receives wireless signals. As occasion demands, the location information module may perform a function of another module among the communication modules to obtain data on the terminal 100 location in substitution or addition. The location information module is used to obtain the terminal 100 location (or current location), but is not limited to a module that directly calculates or obtains the terminal 100 location. This location information module may be mounted in the terminal 100 instead of in the computing device 150, and provide location information from the terminal 100 to a computing device 150.

In addition, the computing device 150 may further include a data extraction module (not illustrated), and this also may be realized as a component of a processor 220. The data extraction module may extract/derive the data required for brain neurodevelopmental prediction service according to the present disclosure, from the information from a terminal 100 or external source received via communication modules.

A processor 220 controls the operations of all the components of the computing device 150 and may perform various functions related to brain neurodevelopment predictions by using memory 210 that stores data of various algorithms or programs that reproduce algorithms, and the data stored in the memory 210, that may be used in the process.

To provide a brain neurodevelopment prediction service, the processor 220 may generate a brain neurodevelopment prediction model based on the data collected from at least one or more of the previously described sources (and terminal 100). Here, Big Data and Artificial Intelligence technology may be used to generate this brain neurodevelopmental prediction model. For example, training data set may be configured based on the data collected from at least one or more sources. Through this, a brain neurodevelopment prediction model may be generated and learned.

Figure 3:
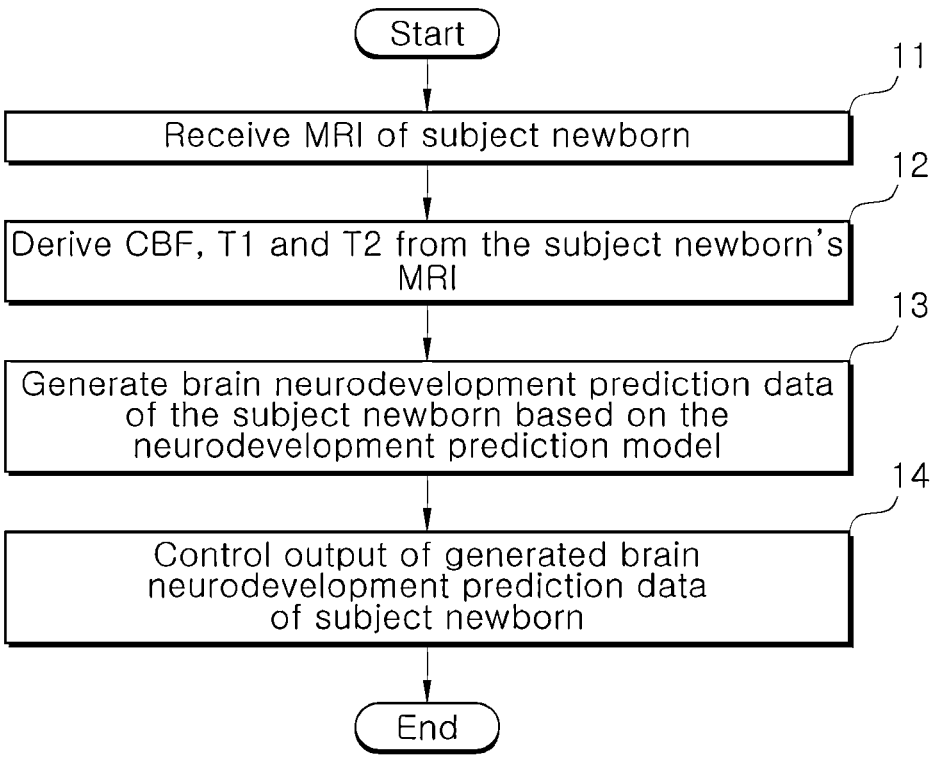
FIG. 3 is a flow chart illustrating the method of brain neurodevelopment prediction according to an exemplary embodiment of the present disclosure.
Figure 4:
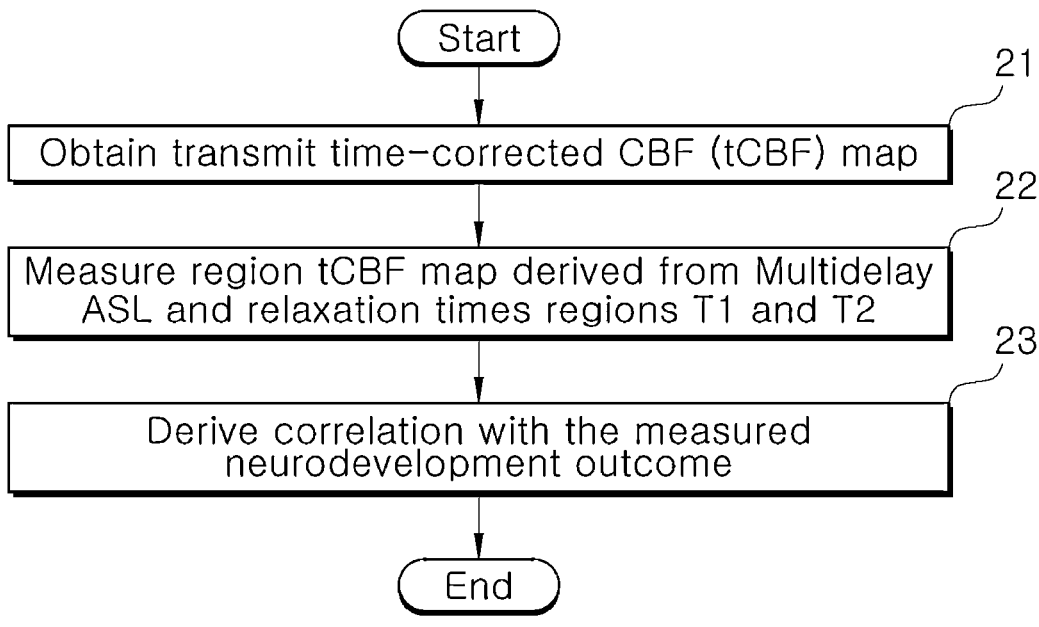
FIG. 4 is a diagram schematically illustrating a method of generating a brain neurodevelopment prediction model according to an exemplary embodiment of the present disclosure.
Figure 5:
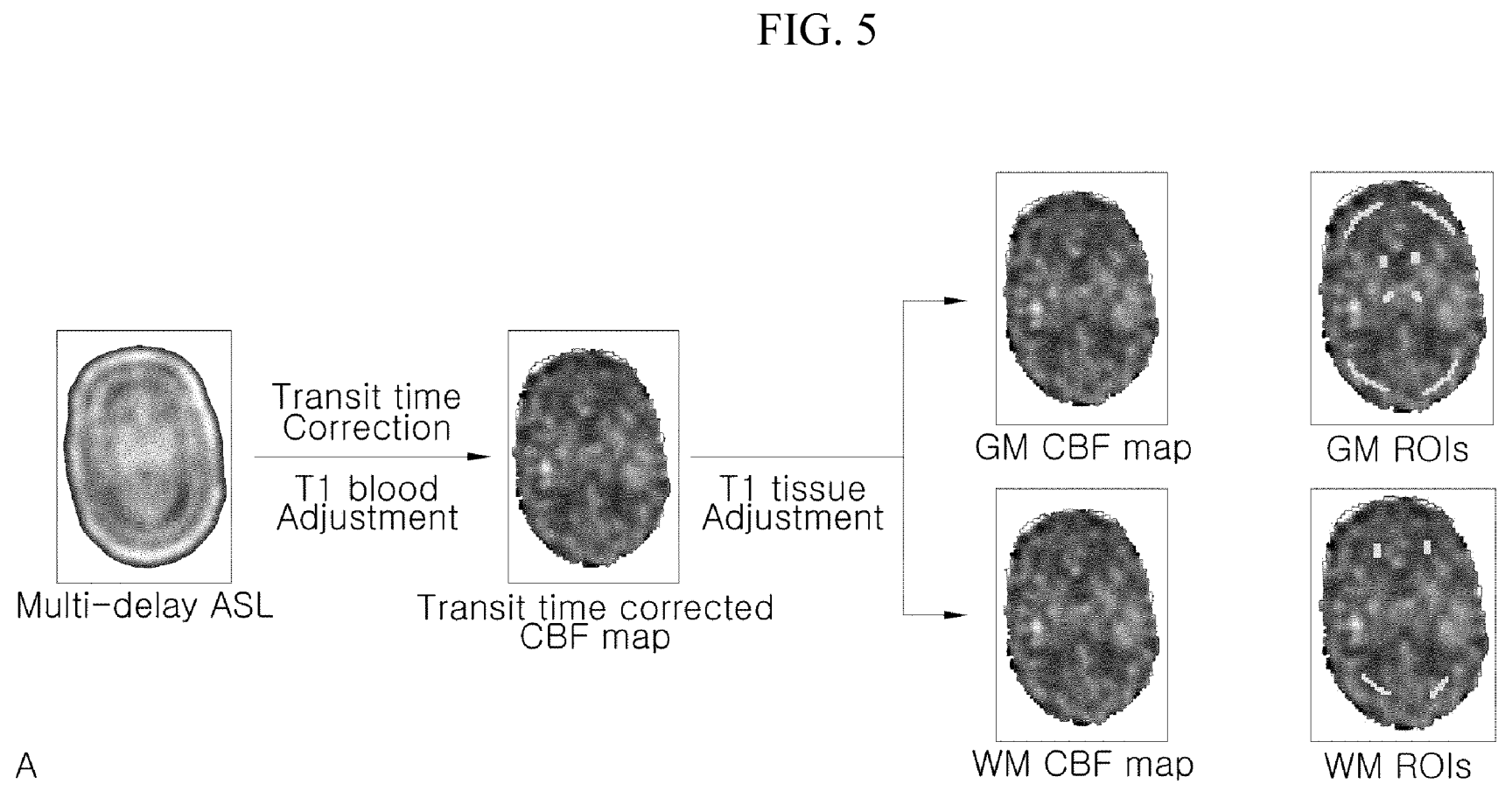
Figure 6:
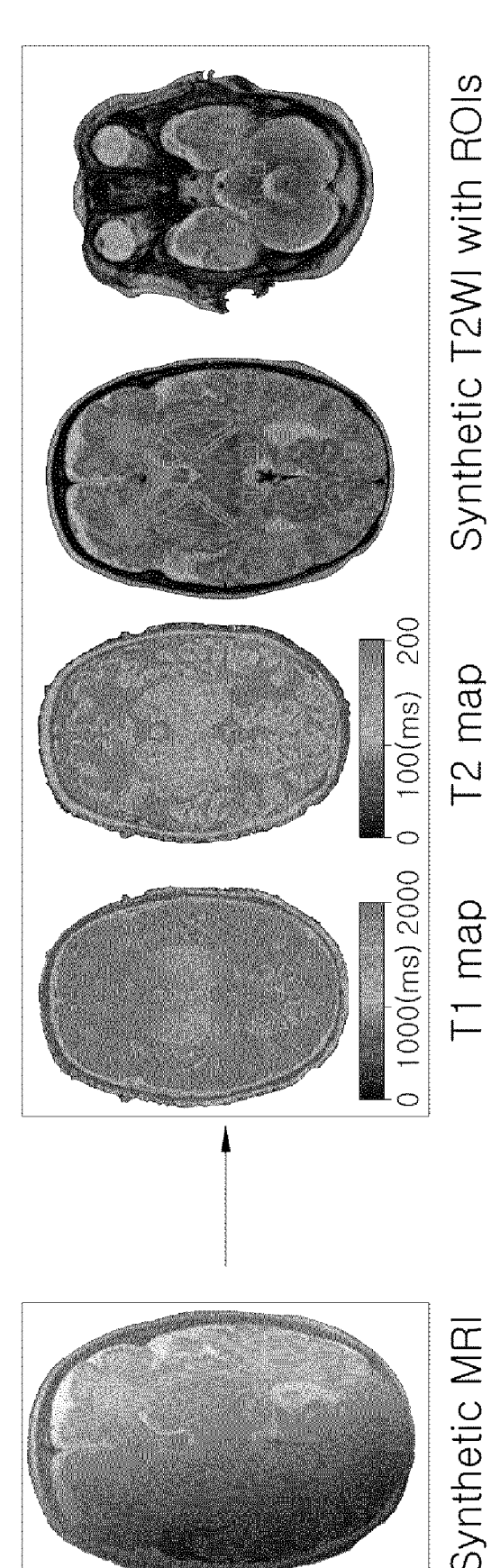
FIG. 6 is a diagram schematically illustrating the relaxation times of brain tissues T1 and T2 according to an exemplary embodiment of the present disclosure.
Figure 11A:
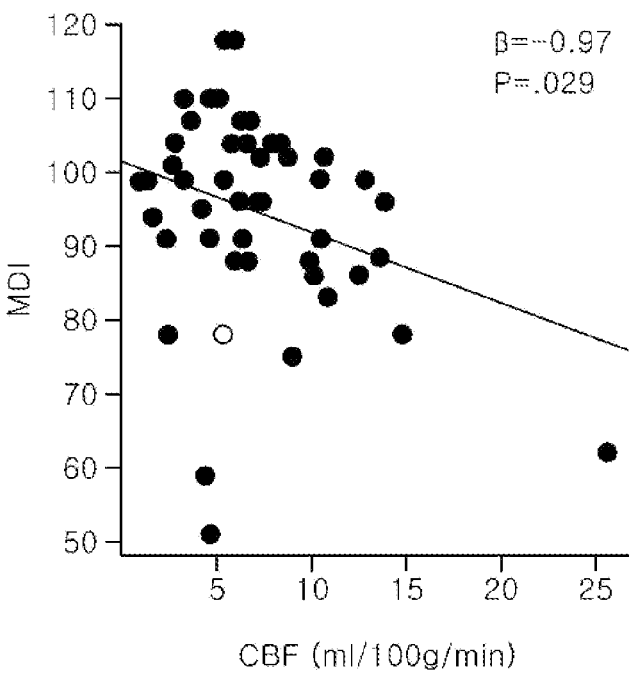
FIGS. 11A and 11B are diagrams schematically illustrating the correlation of the mental development index (MDI) to the present disclosure.
Figure 11B:
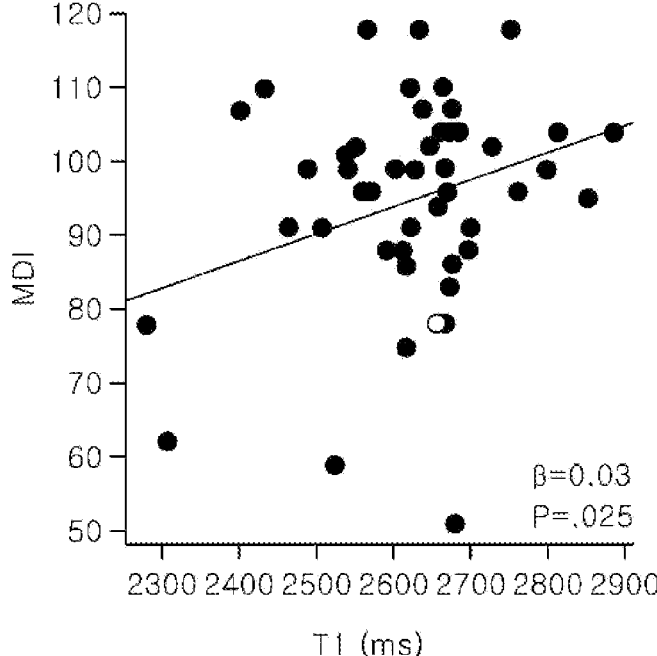
Figure 12:
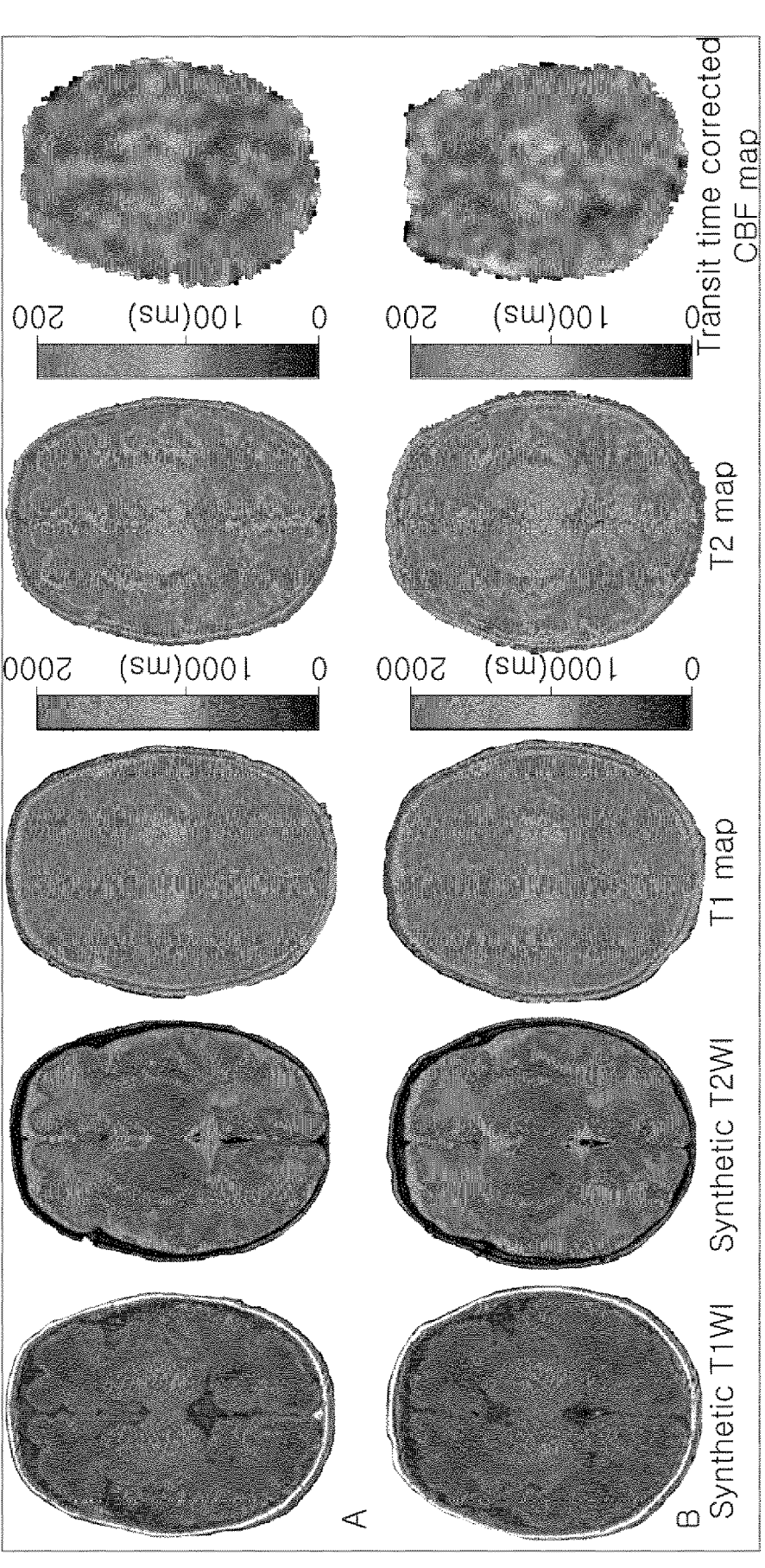
FIG. 12 is a diagram schematically illustrating typical synthetic T1W1, synthetic T2W1, T1 relaxation time map, T2 relaxation map, and tCBF map, according to the present disclosure.

FIG. 3 is a flow chart illustrating the method of brain neurodevelopmental prediction according to an exemplary embodiment of the present disclosure. FIG. 4 is a diagram schematically illustrating a method of generating a brain neurodevelopment prediction model according to an exemplary embodiment of the present disclosure. FIG. 5 is a diagram schematically illustrating cerebral blood flow (CBF) according to an exemplary embodiment of the present disclosure. FIG. 6 is a diagram schematically illustrating the relaxation times of brain tissues T1 and T2 according to an exemplary embodiment of the present disclosure. FIG. 7 to FIG. 10 are diagrams schematically illustrating data related to brain neurodevelopment prediction according to an embodiment of the present disclosure. FIGS. 11A and 11B are diagrams schematically illustrating the correlation of the mental development index (MDI) to the present disclosure. FIG. 12 is a diagram schematically illustrating typical synthetic T1W1, synthetic T2W1, T1 relaxation time map, T2 relaxation map, and tCBF map, according to the present disclosure.

Operations illustrated in FIG. 3 and FIG. 4 may be performed by the computing device 150 of FIG. 1 (in particular, processor 220 of FIG. 2), and are described in this respect. However, the present disclosure is not limited thereto.

According to another exemplary embodiment of the present disclosure, the operations illustrated in FIG. 3 and FIG. 4 may be operated differently from the illustration or performed simultaneously.

First, the method for prediction of a brain neurodevelopmental prognosis is described according to an exemplary embodiment of the present disclosure.

In operation 11, the computing device 150 may receive MRI of a subject newborn.

Here, the computing device 150 may receive the MRI from the subject newborn from terminal 100. On the other hand, the computing device 150 may receive brain neurodevelopmental prediction requests of the subject newborn, as well as the MRI of the subject newborn. Here, the brain neurodevelopmental prediction request of the subject newborn from terminal 100 may be substituted by the MRI of the subject newborn.

In operation 12, the computing device 150 may extract CBF and the brain tissue relaxation times T1 and T2 from the MRI received from the subject newborn.

In operation 13, the computing device 150 may generate the grain neurodevelopment prediction data of the subject newborn using the pregenerated brain neurodevelopment prediction model.

In operation 14, the computing device 150 may control the output from terminal 100 of the generated brain neurodevelopment prediction data of the subject newborn 100.

FIG. 4 illustrates an algorithm generating a brain neurodevelopment prediction model at the computing device 150 according to an exemplary embodiment of the present disclosure. Such a brain neurodevelopment prediction model may be generated prior to or simultaneously with the brain neurodevelopment prediction request of the subject newborn of FIG. 3 to provide corresponding result data.

Referring to FIG. 4, the computing device 150 may obtain the transmission time-corrected tCBF map information as in operation 21, for example, as illustrated in FIG. 5. Here, the transit time-corrected tCBF map information may be performed within a predefined scanning time, using Multidelay ASL which utilizes ASL encoding method.

Here, referring to FIG. 5, all of the frontal lobe WM, occipital lobe WM, frontal lobe cortex GM, and occipital lobe GM location maps may be obtained by adjusting the TI tissue from the acquired tCBF map.

In operation 22, the computing device 150 may measure the region tCBF map derived from a Multidelay ASL and the regions T1 and T2 relaxation times, as illustrated in FIG. 6. Here, the measured region tCBF map derived from the Multidelay ASL and the regions T1 and T2 relaxation times may be performed using MRI.

In operation 23, a computing device 150 may derive the correlation between the measured neurodevelopmental outcome and the MDI (for example, FIGS. 11A and 11).

FIG. 11A, illustrates a correlation graph from the MDI and CBF (for example, R is −0.97 and P is 0.029).

Referring to the FIG. 11A, it may be seen that as the CBF value increases, the correlation with the MDI decreases, i.e., the correlation disappears. For example, in FIG. 11A, when the CBF value is 15 ml/100 g/min or more, the correlation with the MDI becomes relatively lower, so it may be inferred that it is unreliable. In this case, it may be recommended not to re-measure the CBF value nor use the brain neurodevelopment prediction model.

FIG. 11 illustrates the correlation graph between the MDI and the brain tissue relaxation time T1 (for example, R is 0.03 and P is 0.025).

Referring to FIG. 11B, it may be seen that the correlation with the MDI increases as the brain tissue relaxation time T1 increases. Conversely, it may be seen that the correlation with the MDI decreases as the brain tissue relaxation time TI decreases, i.e., the correlation disappears.

For example, in FIG. 11B, when the brain tissue relaxation time T1 is less than 2500 ms, the correlation with the MDI becomes relatively lower, so it may be inferred that it is unreliable. In this case, it may be recommended not to re-measure the CBF value nor use the brain neurodevelopment prediction model.

On the other hand, in FIGS. 11A and 11, by setting a reliable reference value as a threshold, on the CBF value and brain tissue relaxation time TI value, respectively, it may be decided whether to use the brain neurodevelopment prediction model according to an embodiment of the present disclosure by comparison with the threshold.

In addition, when the CBF value and the brain tissue relaxation time T1 value are more than the threshold defined above, for example, the reliability may be decided to adjust and control the use times of the brain neurodevelopment prediction model. For instance, if the CBF value and the brain tissue relaxation time T1 value are more than a threshold or fall in a first reliability interval, the brain neurodevelopment prediction model may be controlled to be used immediately as prediction outcome data of the brain neurodevelopmental prognosis. If the value falls in a second reliability interval, the brain neurodevelopment prediction model may be controlled to be used more than at least twice to use as the prediction outcome data of the brain neurodevelopmental prognosis. In the latter case, if the same outcomes are obtained when used multiple times, it may be used as the prediction outcome data. If the same outcomes are not obtained, an average value may be used or processed another way.

Other than that, the value of the correlation between the previously described CBF value and brain tissue relaxation time TI, and the MDI, may be decided depending on the settings of the computing device 150 or terminal 100. In this case, the terminal 100 user may be a specialist, for example, a medical institution or a licensed physician.

On the other hand, according to an exemplary embodiment of the present disclosure, the MDI is described in FIGS. 11A and 11B, and this disclosure is based on Bayley Scales of infant and toddler development at 18 months of age, but the present disclosure is not limited thereto. Accordingly, different brain neurodevelopmental prediction models may be generated according to the reference data of the MDI.

The computing device 150 may generate and update the brain neurodevelopment prediction model by performing the operations illustrated in FIG. 5.

In other words, the computing device 150 may receive the MRI of a newborn from at least one source, extract CBF and brain tissue relaxation times T1 and T2 from the received MRI, match the extracted data and MDI to derive a correlation therebetween, and generate a brain neurodevelopment prediction model based on the derived correlation.

As previously described, the computing device 150 may store multiple MRIs received via the at least one source, CBF and brain tissue relaxation times T1 and T2 data extracted from the received MRI, data on the brain neurodevelopment prediction model generated based on the derived correlation, and the MRI of the subject newborn and the brain tissue relaxation times T1 and T2 extracted therefrom.

On the other hand, related to generating the brain neurodevelopmental prediction model and extracting correlation, demographic data, materials such as socioeconomic status, and neurodevelopmental outcomes of all newborns illustrated in FIG. 7, The correlation between measurements of the brain region and gestational age illustrated in FIG. 8, regression analysis showing the association between the measured variables and MDI scores illustrated in FIG. 9, and regression analysis showing the association between the measured variables and PDI scores illustrated in FIG. 10 may be referred to.

Referring again to FIGS. 11A and 11, the cognitive results indicate a correlation between CBF T1 relaxation time values in the frontal lobe white matter. One preterm infant showed ventricular dilation (○), and the rest showed no noticeable abnormality (●).

FIG. 12 illustrates typical synthetic T1W1, synthetic T2W1, T1 relaxation time map, T2 relaxation time map and tCBF map of two premature infants.

Referring to FIG. 12, it may be seen that both of the two newborns do not exhibit any evident structural WM abnormality. It shows that a preterm infant whose MDI score is 118 shows frontal WM tCBF of 10 mL/10 g per minute and T1 relaxation time of 2790 ms (A). On the other hand, a preterm infant with a lower MDI score exhibits a relatively higher frontal WM tCBF of 12 mL/100 g per minute and a relatively lower T1 relaxation time of 2704 ms (B).

According to an embodiment of the present disclosure described above, based on the association between the neonatal brain data, including that of premature infants using advanced imaging techniques, the neurodevelopment outcome of newborns including premature infant may be predicted, therefore, to allow a response to be made in a timely manner so that damage or sequelae caused by neurodevelopmental disorders may be eliminated or minimized. In addition, according to the present disclosure, it may be extended and applied to the neurodevelopment of newborns and young children in the medical field to predict early.

The method or steps of algorithms described related to an exemplary embodiment of the present disclosure may be directly realized in hardware, realized as a software module executed by hardware, or realized by a combination thereof. A software module may be stationed on a Random Access Memory (RAM), a Read Only Memory (ROM), an Erasable Programmable ROM (EPROM), an Electrically Erasable Programmable ROM (EEPROM), a flash memory, a hard disk, a removable disk, a CD-ROM, or in any form of computer-readable recording medium well known in the art to which this disclosure pertains.

The above description is only exemplary, and it will be understood by those skilled in the art that the disclosure may be embodied in other concrete forms without changing the technological scope and essential features. Therefore, the above-described embodiments should be considered only as examples in all aspects and not for purposes of limitation.

The invention claimed is:

1. A computing device, comprising:
   a memory; and
   at least one processor performing communication with the memory,
   wherein the processor is configured to:
   receive magnetic resonance imaging (MRI) of a subject newborn;
   extract cerebral blood flow (CBF) using Multidelay Arterial Spin Labeling, from the received MRI;
   extract brain tissue relaxation times T1 and T2, from the received MRI;
   match the extracted CBF and the extracted brain tissue relaxation times T1 and T2 with a mental development index (MDI) to derive a correlation;
   generate a brain neurodevelopment prediction model based on the derived correlation;

generate brain neurodevelopment prediction data of the subject newborn, using the brain neurodevelopment prediction model; and control output of the generated brain neurodevelopmental prediction data of the subject newborn, wherein the processor is further configured to:

obtain a cerebral blood flow (tCBF) map with transit time corrected within a predefined scanning time, using the Multidelay Arterial Spin Labeling; and measure a regional cerebral blood flow (rCBF) map derived from the Multidelay Spin Labeling and regional T1 and T2 relaxation times, using the MRI, and wherein the measured rCBF map is used in deriving the correlation.

2. The computing device of claim 1, wherein the processor is further configured to obtain frontal lobe, occipital lobe, frontal lobe cortex, and occipital cortex regional maps, from the obtained cerebral blood flow (tCBF) map.

3. The computing device of claim 2, wherein the MDI is based on Bayley Scales of infant and toddler development at 18 months of age.

4. The computing device of claim 3, wherein the processor is further configured to control to not re-extract the CBF nor to use the brain neurodevelopment prediction model, in case the CBF extracted from the MRI of the subject newborn is greater than or equal to a first threshold.

5. The computing device of claim 4, wherein the processor is further configured to control to not re-extract the brain tissue relaxations T1 and T2 nor to use the brain neurodevelopment prediction model, in case at least one of the brain tissue relaxations T1 and T2 extracted from the MRI of the subject newborn is less than or equal to a second threshold.

6. The computing device of claim 5, wherein the memory is configured to store multiple MRIs of newborns received, the CBF and brain tissue relaxation times T1 and T2 data extracted from the received MRI, the correlation with the derived MDI, data on the brain neurodevelopment prediction model generated based on the derived correlation, and the MRI of the subject newborn and the CBF and brain tissue relaxation times T1 and T2 data extracted therefrom.

7. The computing device of claim 1, wherein the processor is further configured to generate the brain neurodevelopment prediction data by the brain neurodevelopment prediction model, in case the CBF and the brain tissue relaxation time T1 are greater than a third threshold and fall in a first reliability interval, wherein the processor is further configured to generate the brain neurodevelopment prediction data by using at least twice the brain neurodevelopment prediction model, in case the CBF and the brain tissue relaxation time T1 are greater than the third threshold but at least one of the CBF and the brain tissue relaxation time T1 falls in a second reliability interval, which is different from the first reliability interval, and wherein, in using at least twice the brain neurodevelopment prediction model, when same outcomes are obtained from at least two usages of the brain neurodevelopment prediction model, the same outcomes are used as the brain neurodevelopment prediction data, and when the same outcomes are not obtained from at least two usages of the brain neurodevelopment prediction model, an average value of outcomes is used as the brain neurodevelopment prediction data.

8. A system for prediction of a brain neurodevelopmental prognosis comprising:

a terminal requesting brain neurodevelopment prognosis prediction of a subject newborn; and a computing device, wherein the computing device includes a processor, wherein the processor is configured to:

receive magnetic resonance imaging (MRI) of a subject newborn;

extract cerebral blood flow (CBF) using Multidelay Arterial Spin Labeling, from the received MRI;

extract brain tissue relaxation times T1 and T2, from the received MRI;

match the extracted CBF and the extracted brain tissue relaxation times T1 and T2 with a mental development index (MDI) to derive a correlation;

generate a brain neurodevelopment prediction model based on the derived correlation;

generate brain neurodevelopment prediction data of the subject newborn using the brain neurodevelopment prediction model; and control output of the generated brain neurodevelopment prediction data of the subject newborn, wherein the processor is further configured to:

obtain a cerebral blood flow (tCBF) map with transit time corrected within a predefined scanning time, using the Multidelay Arterial Spin Labeling; and measure a regional cerebral blood flow (rCBF) map derived from the Multidelay Spin Labeling and regional T1 and T2 relaxation times, using the MRI, and wherein the measured rCBF map is used in deriving the correlation.

9. The system of claim 8, wherein the processor is further configured to generate the brain neurodevelopment prediction data by the brain neurodevelopment prediction model, in case the CBF and the brain tissue relaxation time T1 are greater than a third threshold and fall in a first reliability interval, wherein the processor is further configured to generate the brain neurodevelopment prediction data by using at least twice the brain neurodevelopment prediction model, in case the CBF and the brain tissue relaxation time T1 are greater than the third threshold but at least one of the CBF and the brain tissue relaxation time T1 falls in a second reliability interval, which is different from the first reliability interval, and wherein, in using at least twice the brain neurodevelopment prediction model, when same outcomes are obtained from at least two usages of the brain neurodevelopment prediction model, the same outcomes are used as the brain neurodevelopment prediction data, and when the same outcomes are not obtained from at least two usages of the brain neurodevelopment prediction model, an average value of outcomes is used as the brain neurodevelopment prediction data.

10. A method for prediction of a brain neurodevelopmental prognosis, performed by a device, the method comprising:

receiving magnetic resonance imaging (MRI) of a subject newborn;

extracting cerebral blood flow (CBF) using Multidelay Arterial Spin Labeling, from the received MRI;

extracting brain tissue relaxation times T1 and T2, from the received MRI;

matching the extracted CBF and the extracted brain tissue relaxation times T1 and T2 with a mental development index (MDI) to derive a correlation;

generating a brain neurodevelopment prediction model based on the derived correlation;

generating brain neurodevelopment prediction data of the subject newborn using the brain neurodevelopment prediction model;

controlling output of the generated brain neurodevelopment prediction data of the subject newborn;

obtaining a cerebral blood flow (tCBF) map with transit time corrected within a predefined scanning time, using the Multidelay Arterial Spin Labeling; and measuring a regional cerebral blood flow (rCBF) map derived from the Multidelay Spin Labeling and regional T1 and T2 relaxation times, wherein the measured rCBF map is used in deriving the correlation.

11. The method of claim 10, wherein frontal lobe, occipital lobe, frontal lobe cortex, and occipital cortex regional maps are obtained from the obtained cerebral blood flow (tCBF) map.

12. The method of claim 11, wherein the MDI is based on Bayley Scales of infant and toddler development at 18 months of age.

13. The method of claim 12, wherein the method is controlled to not re-extract the CBF nor to use the brain neurodevelopment prediction model, in case the CBF extracted from the MRI of the subject newborn is greater than or equal to a first threshold.

14. The method of claim 13, wherein the method is controlled to not re-extract the brain tissue relaxations T1 and T2 nor to use the brain neurodevelopment prediction model, in case at least one of the brain tissue relaxations T1 and T2 extracted from the MRI of the subject newborn is less than or equal to a second threshold.

15. The method of claim 14, further comprising:

storing multiple MRIs of the newborns received, the CBF and brain tissue relaxation times T1 and T2 data extracted from the received MRI, the correlation with the derived MDI, data on the brain neurodevelopment prediction model generated based on the derived correlation, and the MRI of the subject newborn and the CBF and brain tissue relaxation times T1 and T2 data extracted therefrom.

16. The method of claim 10, wherein generating the brain neurodevelopment prediction data comprises:

generating the brain neurodevelopment prediction data by the brain neurodevelopment prediction model, in case the CBF and the brain tissue relaxation time T1 are greater than a third threshold and fall in a first reliability interval; and generating the brain neurodevelopment prediction data by using at least twice the brain neurodevelopment prediction model, in case the CBF and the brain tissue relaxation time T1 are greater than the third threshold but at least one of the CBF and the brain tissue relaxation time T1 falls in a second reliability interval, which is different from the first reliability interval, and wherein, in using at least twice the brain neurodevelopment prediction model, when same outcomes are obtained from at least two usages of the brain neurodevelopment prediction model, the same outcomes are used as the brain neurodevelopment prediction data, and when the same outcomes are not obtained from at least two usages of the brain neurodevelopment prediction model, an average value of outcomes is used as the brain neurodevelopment prediction data.

* * * * *